(12) United States Patent
Belleville et al.

(10) Patent No.: US 7,689,071 B2
(45) Date of Patent: Mar. 30, 2010

(54) FIBER OPTIC PRESSURE SENSOR FOR CATHETER USE

(75) Inventors: Claude Belleville, L'Ancienne-Lorette (CA); Sylvain Bussière, Val-Bélair (CA); Richard Van Neste, Sainte-Foy (CA)

(73) Assignee: Opsens Inc., Quebec, Quebec (CA)

( * ) Notice: Subject to any disclaimer, the term of this patent is extended or adjusted under 35 U.S.C. 154(b) by 590 days.

(21) Appl. No.: 11/138,423

(22) Filed: May 27, 2005

(65) Prior Publication Data

US 2006/0133715 A1 Jun. 22, 2006

Related U.S. Application Data

(60) Provisional application No. 60/637,755, filed on Dec. 22, 2004.

(51) Int. Cl.
 *G02B 6/00* (2006.01)
(52) U.S. Cl. .................................................. 385/13
(58) Field of Classification Search .................... 385/13
 See application file for complete search history.

(56) References Cited

U.S. PATENT DOCUMENTS

| | | | |
|---|---|---|---|
| 4,274,423 A | 6/1981 | Mizuno et al. | |
| 4,576,181 A | 3/1986 | Wallace et al. | |
| 4,678,904 A | 7/1987 | Saaski et al. | |
| 4,771,782 A | 9/1988 | Millar et al. | |
| 5,105,665 A * | 4/1992 | Parsons et al. | 73/704 |
| 5,385,053 A * | 1/1995 | Wlodarczyk et al. | 73/705 |
| 5,392,117 A | 2/1995 | Belleville et al. | |
| 6,738,145 B2 * | 5/2004 | Sherrer et al. | 356/480 |
| 7,173,713 B2 * | 2/2007 | Xu et al. | 356/480 |
| 2002/0003917 A1 * | 1/2002 | Sherrer et al. | 385/12 |
| 2002/0159671 A1 * | 10/2002 | Boyd et al. | 385/12 |
| 2002/0183597 A1 | 12/2002 | Kaufman et al. | |
| 2004/0244502 A1 | 12/2004 | Youngner et al. | |
| 2005/0062979 A1 | 3/2005 | Zhu et al. | |
| 2005/0157305 A1 * | 7/2005 | Yu et al. | 356/480 |
| 2005/0183507 A1 | 8/2005 | Bailey et al. | |
| 2007/0081165 A1 * | 4/2007 | Kilic et al. | 356/477 |

OTHER PUBLICATIONS

U.S. Appl. No. 10/829,980, filed Oct. 27, 2005, Belleville.
U.S. Appl. No. 60/610,950, Duplain.
Tohyama et al., "A Fiber-Optic Pressure Microsensor for Biomedical Applications", *1997 International Conference on Solid-State Sensors and Actuators*. Chicago, Jun. 16-19, 1997, (Jun. 16, 1997), p. 1489, right col., line 11 to p. 1490, right col., line 4; Fig. 1.

(Continued)

*Primary Examiner*—Uyen-Chau N Le
*Assistant Examiner*—Hoang Tran
(74) *Attorney, Agent, or Firm*—C Marc Benoit; Benoit & Cote SENC

(57) ABSTRACT

The invention provides a miniature robust fiber optic pressure sensor. The miniature fiber optic sensor comprises a Fabry-Perot chip bonded to an optical fiber. The invention provides a new sensor design that reduces the amount of adhesive required to bond the optical fiber to the Fabry-Perot sensor such that the sensor is less sensitive to moisture. The invention also provides manufacturing methods of the sensor comprising a method based on etching and a method based on using an excimer laser. The invention also provides a chip design that renders the chip less sensitive to thermal changes. The invention also provides a chip design in which a sensor diaphragm has a well-defined thickness. The invention also provides a chip design that protects the chip from etching.

15 Claims, 9 Drawing Sheets

OTHER PUBLICATIONS

Tohyama et al.. "A Fiber-Optic Silicon Pressure Sensor for Ultra-Thin Catheters", *The 8th International Conference on Solid-State Sensors and Actuators, and Eurosensors IX*, Stockholm, Sweden, Jun. 25-29, 1995 (Jun. 25, 1995), p. 596, right col., line 1 to p. 598, left col., line 8, Fig. 3, 4.

Kim et al, "Micromachined Fabry-Perot Cavity Pressure Transducer with Optical Fiber Interconnects", *SPIE Micromachined Devices and Components*, Austin TX, Oct. 23-24, 1995 (Oct. 23, 1995), pp. 242-249, p. 243, line 9 to p. 245, line 20, Fig. 1, 2.

* cited by examiner

FIBER OPTIC PRESSURE SENSOR FOR CATHETER USE

CROSS-REFERENCE TO RELATED APPLICATIONS

This application claims priority under 35USC§119(e) of U.S. provisional patent application 60/637,755 filed Dec. 22, 2004, the specification of which is hereby incorporated by reference.

FIELD OF INVENTION

The invention relates to pressure sensor for in-vivo measurements and more specifically, to catheter tip fiber optic pressure sensor.

BACKGROUND OF THE INVENTION

The use of catheters is sharply increasing in a number of diagnostic and therapeutics procedures, leading to less invasive diagnostics and therapy. It is often required to perform pressure measurement of internal tissues or fluids. It is always of the utmost importance to have the capability of reducing the size of the catheter and thus, the pressure sensor must be as small as possible. Other important features for a pressure sensor are fidelity and stability.

Among the first invasive pressure sensors used in combination with catheters were external and were connected to internal body pressure by way of fluid filled tubing as described in U.S. Pat. No. 4,576,181, Wallace et al., 1986. This method suffers however from its extreme sensitivity against tubing movement which strongly affect the fidelity of the pressure measurement. In addition, for the tubing to properly transmit the dynamic of the pressure, it must be relatively large which provides poor compatibility with actual catheter design.

This important issue has been resolved with catheter tip pressure sensors such as those taught by U.S. Pat. No. 4,274,423, Mizuno et al., 1981 and U.S. Pat. No 4,771,782., Millar et al., 1988. These sensors can be made to fit into fairly small catheters without suffering from the sensitivity to catheter or patient movement. On the other hand, their use is limited to areas where no electromagnetic noise is present, such as in presence of MRI or electrosurgery. Another drawback of those electrical sensors is their sensitivity to moisture drift that results from the change of the conductivity of the media surrounding the pressure chip.

Fiber optic sensors have the potential of resolving those problems. Some initial design such as the one described by Matsumoto et al., "The development of a fibre optic catheter tip pressure transducer", Journal of Medical Engineering & Technology, Vol. 2, no. 5 (1978) were based on the variation of the light intensity induced by various mechanism. Those sensors are well known to be prone to fluctuations due to all sort of environmental effects.

In the past few years, there have been an increasing number of fiber optic sensors based on the use of a Fabry-Perot cavity as the sensing element. Fabry-Perot sensors can be configured in various ways, such that they can measure a variety of parameters. In addition, it is possible to make low cost, miniature Fabry-Perot sensors by way of micromachining techniques (MEMS).

A variety of techniques have been proposed for interrogating a Fabry-Perot cavity. U.S Pat. No. 5,392,117, U.S. patent Filing Ser. No. 10/829,980 and U.S. Pat. Filling No. 60/610,950 are good examples of such interrogation techniques that have the ability to accurately measure a Fabry-Perot cavity length, i.e. the distance separating the two mirrors. It is worth mentioning that those interrogation methods are extremely accurate and reliable and thus, the final accuracy and repeatability of a Fabry-Perot pressure sensors used in combination with such an interrogation technique will strongly depend on the quality of the sensor itself.

Fabry-Perot based pressure sensors are then considered as those having the best potential to suit the needs for catheter tip pressure measurement. U.S. Pat. No. 4,678,904, Saaski et al., 1987 teaches one method of producing a Fabry-Perot sensor that has some very interesting characteristics. Although it can be produced at a fairly low cost while achieving good reproducibility, attaching the chip on tip of an optical fiber still have to be considered. For instance, bonding the pressure chip using solder glass makes the process very expensive, raising the cost to a level not compatible with medical uses. The pressure chip could be bonded on tip of the optical fiber using a polymer, but the cost would remain high because the tip of the fiber optic under this circumstance needs to be processed to receive the chip. For the chip to be well attached to the fiber, the fiber needs to be enlarged to a size comparable to the pressure chip with the addition of a tube. Notwithstanding the additional cost, the use of a polymer nearby the Fabry-Perot cavity makes this design prone to moisture induced drifting due to adhesive swelling.

Improvement to the previous design has been made by putting into practice the concept of chip level packaging. Gander et al. "Embedded micromachined fiber-optic Fabry-Perot pressure sensors in aerodynamics applications", IEEE Sensors Journal, Vol. 3, No. 1 (2003) teaches a method of producing a pressure chip that includes an opening for accommodating the optical fiber, thus eliminating the need for additional fiber optic processing. On the other hand, this design can in no circumstance provide any stable pressure measurement. Since the tip of the optical fiber constitutes the first mirror of the Fabry-Perot cavity, the pressure measurement becomes functions of any fiber optic unavoidable pistoning due to moisture, temperature and handling.

Although the paper presented by Tohyama et al., "A fiber-optic pressure microsensor for biomedical applications", Sensors and actuators, A66 (1998) disclosed a method of producing an intensity based pressure sensor, it teaches the use of a small silicon funnel produced on the chip level for accommodating the optical fiber. Kim et al., "Micromachined Fabry-Perot cavity pressure transducer with optical fiber interconnects", SPIE Vol. 2642, (1995) teaches a similar concept, but using instead a Fabry-Perot cavity as the optical element. One important drawback of this method remains its sensitivity to moisture drift. It is known that polymers are swelling in presence of humidity. Upon swelling, the polymer that fills the silicon funnel for holding the optical fiber in place will induce a bending force to the pressure chip that brings the mirrors in closer proximity and thus, inducing drift.

FIG. 1 shows a prior art construction of a Fabry-Perot sensor 10 for measuring pressure. A bi-directional fiber optic 9 guides the light signal 7 toward a Fabry-Perot pressure chip 21. The pressure chip 21 is made of from a glass substrate 1. One first partially reflective mirror 2 is deposited within a recessed cavity 5 performed on the top surface of the glass substrate 1. A second deformable mirror 3 is bonded or welded to the glass substrate 1. Both mirrors 2, 3, spaced by a distance given by the depth of the recessed cavity 5, constitutes a Fabry-Perot cavity 6. The second mirror 3 bows toward first mirror 2 as function of an applied pressure. FP cavity length 6 is then an unambiguous function of pressure. The deflection of the diaphragm as a function of the pressure is usually of the order of 2 nm/mmHg. To be integrated into a catheter, the pressure chip 21 needs to be packaged so that the light signal travelling into the optical fiber 9 is directed from the fiber to the Fabry-Perot cavity 6, and back to the optical fiber 9. Although the use of an optical lens 8 can be considered, this does not yet resolve the method for attaching the fiber 9 to the glass substrate so that no environmental parasitic effect will be detrimental to the pressure measurement.

FIG. 2 illustrates another prior art where the fiber optic 9 is brought in close proximity to the Fabry-Perot cavity 6, usually less than 200 microns, so that no optical system is needed to bring the light in and out of the Fabry-Perot cavity 6. The presence of the adhesive 11 directly on the back side 12 of the glass substrate 1 makes this design very sensitive to moisture induced drift. Also, the insertion of the optical fiber 9 into the tube 13 contributes increasing the production cost.

FIG. 3A shows another prior art design where the method for assembling the fiber optic 9 to the pressure chip 21 is achieved at the chip level. The production cost is thus fairly acceptable. By preferential etching of silicon with methods well know by those skilled in the art, it is possible to micromachine funnels 22 into silicon substrate. With a (100) oriented silicon substrate, funnels with angles of 54 degrees are achieved. To adequately bond the fiber optic 9 into the funnel 22, it is required to completely fill the funnel with an adhesive 23. Considering the amount of adhesive required to fill a funnel with such a wide opening, the moisture induced swelling of the adhesive 23 will induce a strong bending moment 24, as illustrated by FIG. 3B, sufficient to bend the pressure chip so that the diaphragm 25 significantly deflects toward the glass surface 26, resulting in a pressure drift. Because the funnel is wide open, the pulling force required to pull the pressure chip off the fiber is significantly reduced.

Thus one drawback of current Fabry-Perot pressure sensors is their sensitivity to moisture.

Another drawback of Fabry-Perot pressure sensors is their sensitivity to temperature. For the sensors to find practical uses in medical fields, it is of importance to provide a method for compensating thermal shift that occurs as a result of the differences in the coefficient of thermal expansion of materials used to build the sensor.

Another drawback of the actual sensors is the variation in their sensitivity when immersed into a water based solution, phenomenon usually erroneously associated to moisture drift.

SUMMARY

The invention provides a miniature robust fiber optic pressure sensor that can be produced at a fairly low cost, delivering high fidelity measurements and low thermal shift, while not being prone to moisture drift. The miniature fiber optic sensor comprises a Fabry-Perot chip bonded to an optical fiber. The invention provides a new sensor design that reduces the amount of adhesive required to bond the optical fiber to the Fabry-Perot sensor such that the sensor is less sensitive to moisture. The invention also provides manufacturing methods of the sensor comprising a method based on etching and a method based on using an excimer laser. The invention also provides a chip design that renders the chip less sensitive to thermal changes. The invention also provides a chip design that provides a sensor diaphragm having a well-defined thickness. The invention also provides a chip design that protects the chip from etching.

The invention provides a Fabry-Perot pressure chip for use as a pressure sensor when interfaced to an optical fiber, the chip comprising a body comprising a first surface; and a diaphragm covering the first surface and affixed to the body, the diaphragm defining a second surface; the first and second surfaces being separated by a distance and forming a Fabry-Perot cavity; the body comprising a second cavity for receiving an extremity of said optical fiber and securing said optical fiber therein, the second cavity having a form closely matching the inserted extremity, whereby a small quantity of adhesive is required to secure the inserted extremity within said second cavity. The Fabry-Perot pressure chip further comprises the optical fiber for relaying a light between an optical source and the Fabry-Perot cavity, an extremity of the optical fiber being inserted in the second cavity of the chip and adhesively bound therein, for providing a fiber Fabry-Perot pressure sensor.

The invention also provides a method of manufacturing a Fabry-Perot pressure chip used as a pressure sensor when interfaced to an optical fiber. The method comprises providing a substrate having a bottom face and a top face, the substrate adapted to relay light between the bottom face and the top face; creating a first surface in the top face; mounting, on the top face, a diaphragm having a second surface, said first and second surfaces being separated by a distance and forming a Fabry-Perot cavity; and creating a second cavity in the bottom face having a form closely matching an extremity of said optical fiber. The method further comprises inserting in the second cavity of the chip the extremity of the optical fiber and securing it therein, for manufacturing a fiber Fabry-Perot pressure sensor.

The invention also provides a method of manufacturing a Fabry-Perot pressure chip used as a pressure sensor when interfaced to an optical fiber. The method comprises providing a substrate having a bottom face and a top face, the substrate adapted to relay light between the bottom face and the top face; creating a first surface in the top face; providing a Fabry-Perot body by mounting on the top face and over the first surface, a diaphragm having a second surface, the first and second surfaces being separated by a distance and forming a Fabry-Perot cavity; providing a second substrate having a rear face and a front face, the second substrate for receiving an optical fiber; providing an interface body by creating in the rear face a through hole having a form closely matching an extremity of the optical fiber; and binding the bottom face of the Fabry-Perot body to the front face of the interface body.

The invention also provides a method of manufacturing a Fabry-Perot pressure chip used as a pressure sensor when interfaced to an optical fiber. The method comprises providing a substrate having a bottom face and a top face, the substrate adapted to relay light between the bottom face and the top face; creating a first surface in the top face; and creating a silicon diaphragm mounted to the top face of the substrate by: providing a Silicon-on-Insulator (SOI) wafer having a silicon layer on a $SiO_2$ layer on a silicon substrate, the silicon layer defining a second surface; affixing the SOI wafer to the top face so as to have the second surface facing the first surface; removing the silicon substrate and the $SiO_2$; the first and second surfaces being separated by a distance and forming a Fabry-Perot cavity.

The invention also provides a Fabry-Perot pressure chip for use as a pressure sensor when interfaced to an optical fiber. The chip comprises a body comprising a first surface, the body having a coefficient of thermal expansion (CTE), and a diaphragm covering the first surface and affixed to the body, the diaphragm having an internal and an external surface, the first and internal surfaces being separated by a distance and forming a Fabry-Perot cavity, the diaphragm further comprising a layer of material having a coefficient of thermal expansion different than the CTE of the body, for compensating a deformation of the diaphragm due to a temperature change.

The invention also provides a method of manufacturing a Fabry-Perot pressure chip used as a pressure sensor when interfaced to an optical fiber. The method comprises providing a body having a bottom face and a top face; creating a first surface in the top face; and creating a diaphragm mounted to the top face of the body by: providing a wafer having a diaphragm layer on a substrate and providing a layer of material having a coefficient of thermal expansion (CTE) on at least a portion of the diaphragm layer to provide an overlayed diaphragm layer, the overlayed diaphragm defining a second surface; affixing the wafer to the top face so as to have the second surface facing the first surface and removing the substrate, the first and second surfaces being separated by a distance and forming a Fabry-Perot cavity.

The invention also provides a method of manufacturing a Fabry-Perot pressure chip used as a pressure sensor when interfaced to an optical fiber. The method comprises providing a body having a bottom face and a top face; creating a first surface in the top face; and creating a diaphragm mounted to the top face of the body by: providing a wafer having a diaphragm layer on a substrate, the diaphragm defining a second surface; affixing the wafer to the top face so as to have the second surface facing the first surface and removing the substrate; and providing a layer of material having a coefficient of thermal expansion (CTE) on at least a portion of the mounted diaphragm, the first and second surfaces being separated by a distance and forming a Fabry-Perot cavity.

The invention also provides a Fabry-Perot pressure chip for use as a pressure sensor when interfaced to an optical fiber. The chip comprises a body comprising a first surface, and a diaphragm covering the first surface and affixed to the body, the diaphragm having an internal and an external surfaces, the first and internal surfaces being separated by a distance and forming a Fabry-Perot cavity, the external surface comprising a protective layer against etching.

The invention also provides a method of manufacturing a Fabry-Perot pressure chip used as a pressure sensor when interfaced to an optical fiber. The method comprises providing a body having a bottom face and a top face; creating a first surface in the top face; and creating a diaphragm mounted to the top face of the body by: providing a wafer having a diaphragm layer on a substrate, the diaphragm defining a second surface; affixing the wafer to the top face so as to have the second surface facing the first surface and removing the substrate; and depositing a layer of protection material on the mounted diaphragm, the first and second surfaces being separated by a distance and forming a Fabry-Perot cavity.

DETAILED DESCRIPTION

In the following description of the embodiments, references to the accompanying drawings are by way of illustration of an example by which the invention may be practiced. It will be understood that other embodiments may be made without departing from the scope of the invention disclosed.

Figure 1:
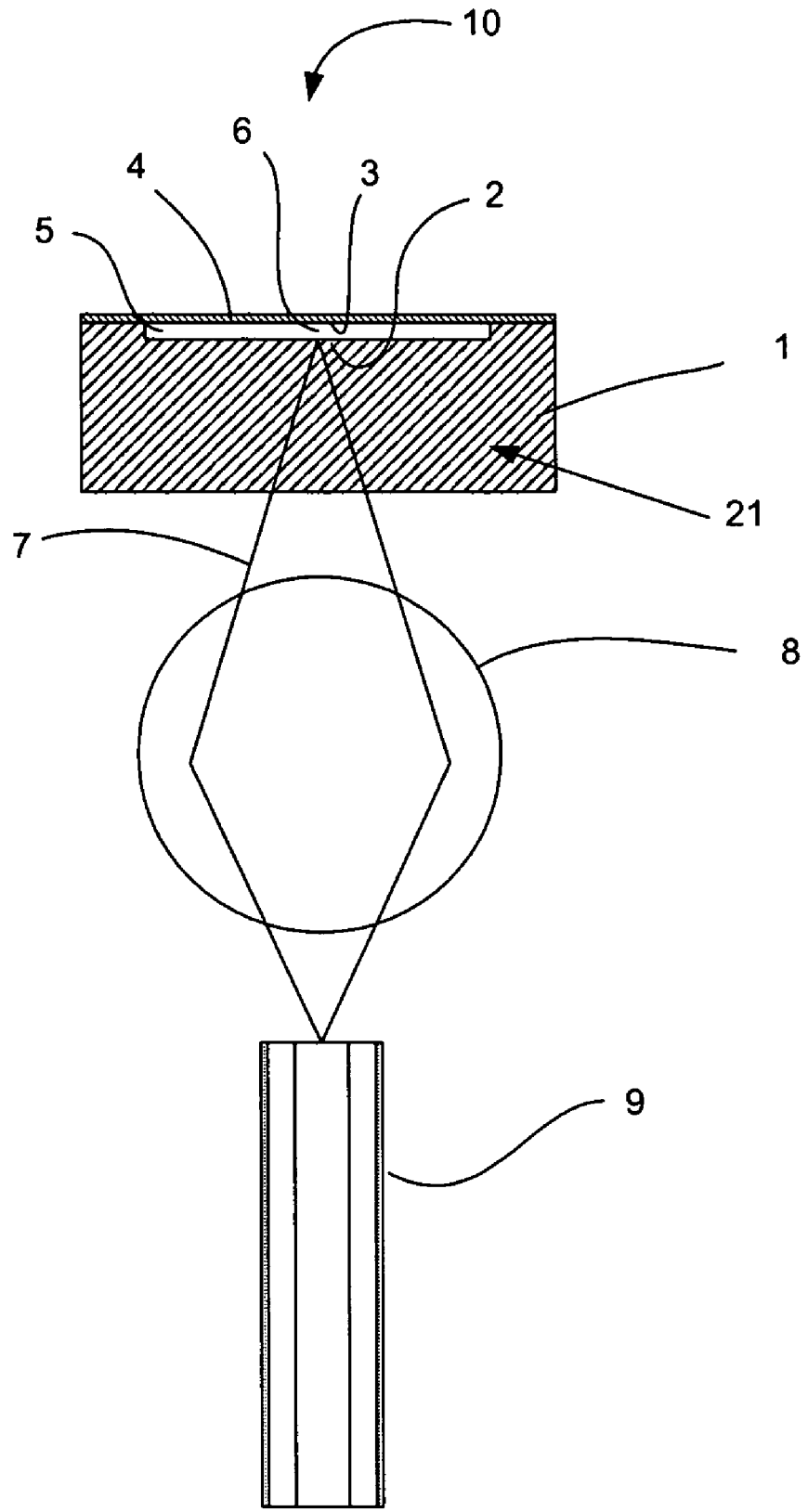
FIG. 1 is a schematic cross-section view of a Fabry-Perot sensor as found in the prior art.
Figure 2:
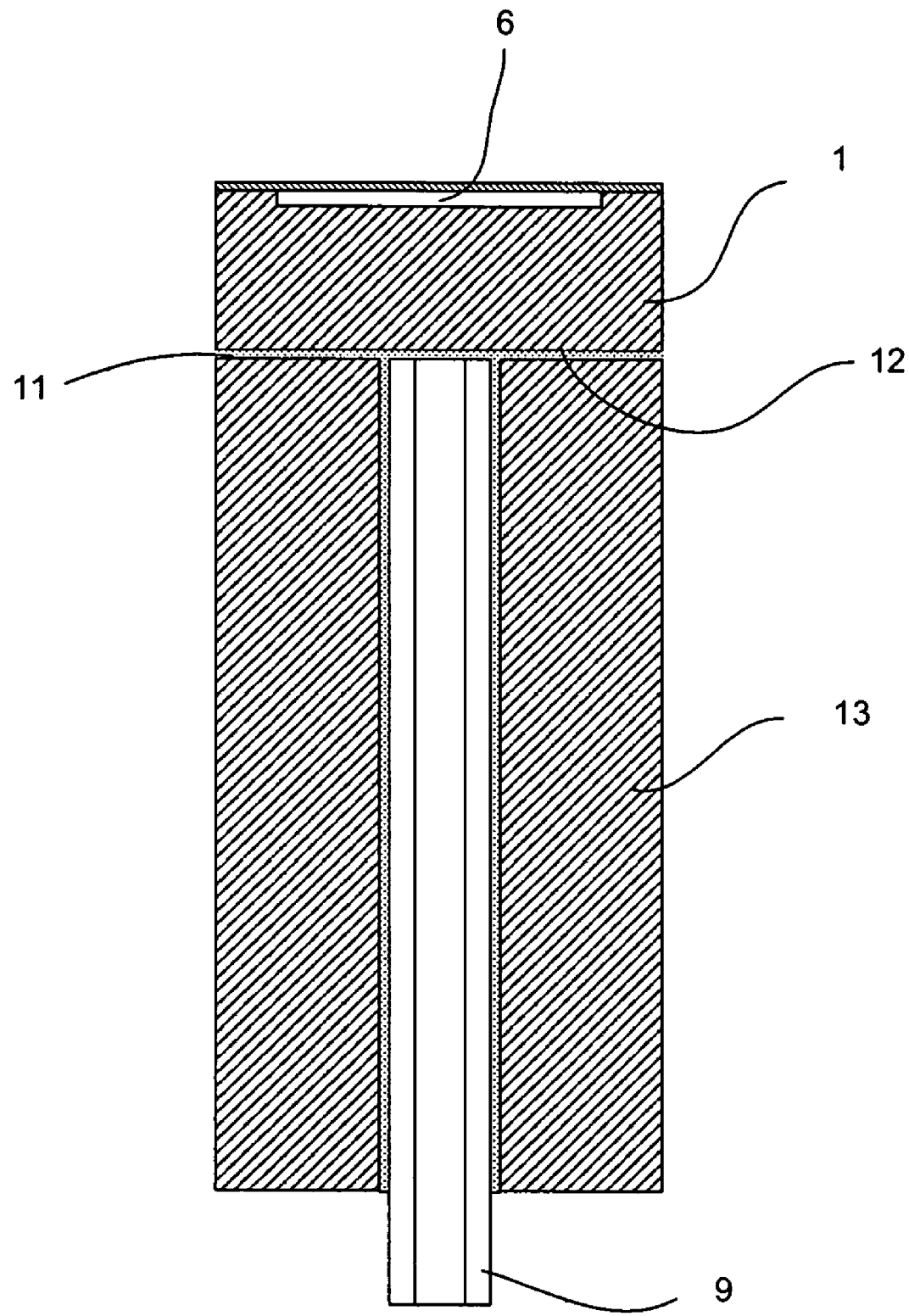
FIG. 2 is a schematic cross-section view of a Fabry-Perot sensor with an embedded optical fiber as found in the prior art.
Figure 3A:
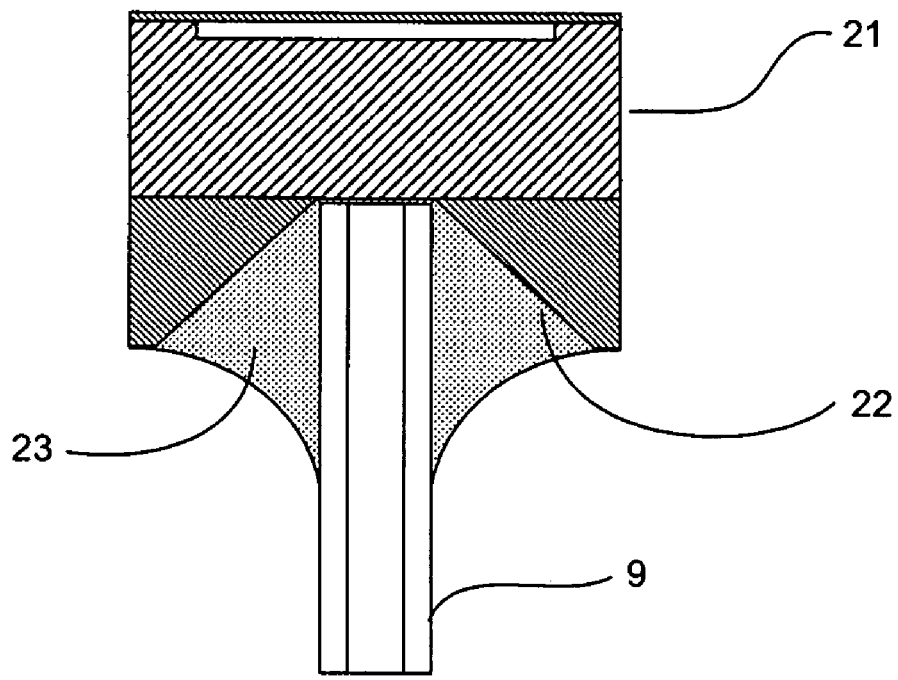
FIGS. 3A and 3B are schematic cross-section views of another Fabry-Perot sensor with an embedded optical fiber as found in the prior art.
Figure 3B:
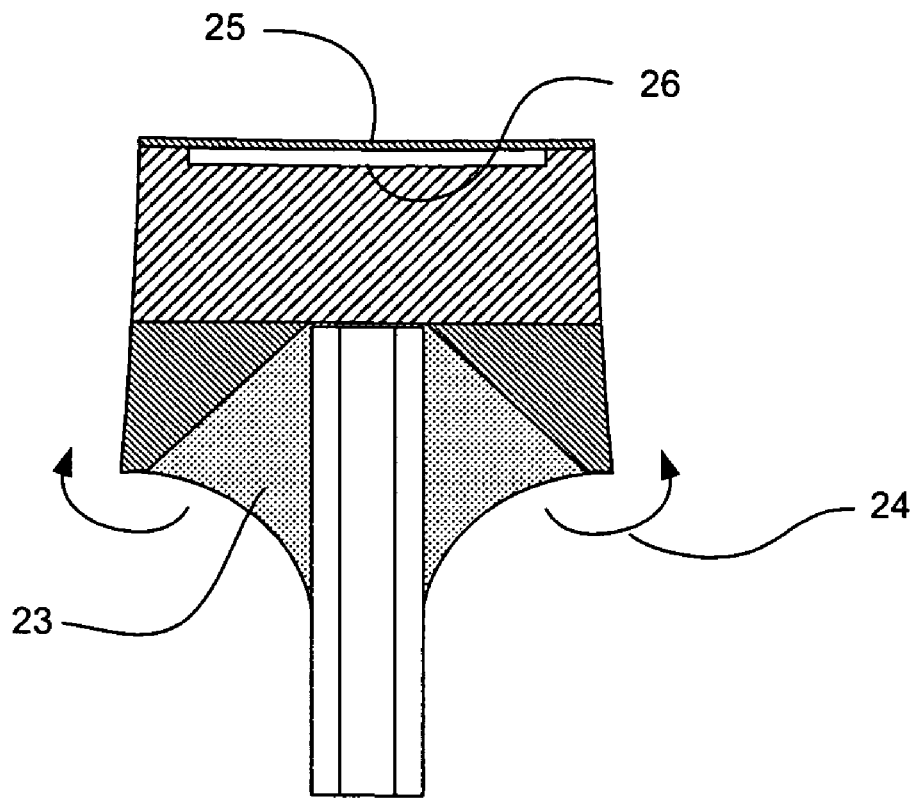
Figure 4:
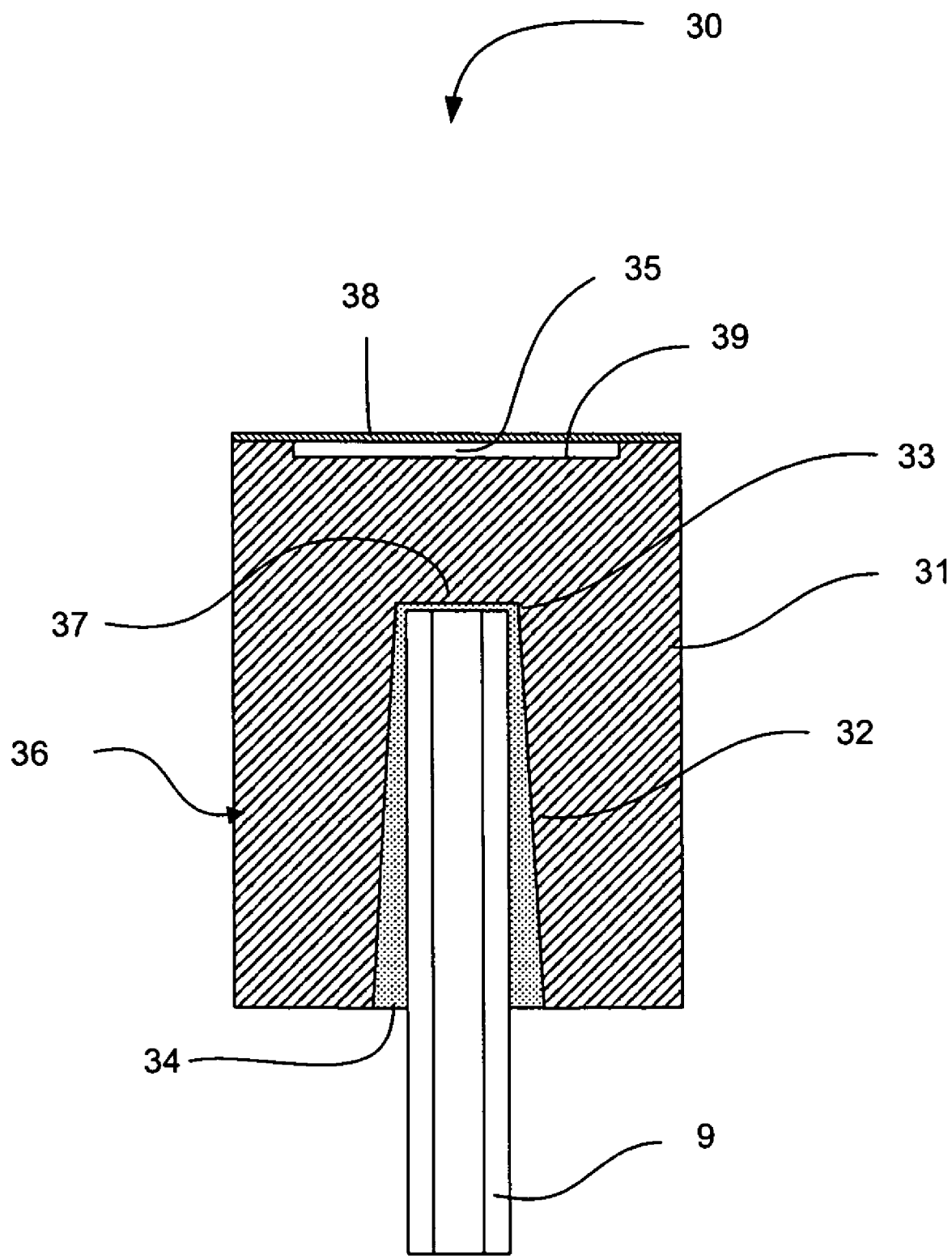
FIG. 4 is a schematic cross-section view of a fiber optic Fabry-Perot pressure sensor, in accordance with a first embodiment of the present invention.

Referring now to FIG. 4, there is shown a fiber optic Fabry-Perot pressure sensor 30, in accordance with a first embodiment of the present invention that is less sensitive to moisture induced drift then prior designs. The sensor 30 comprises a pressure chip 36 that is coupled to an optical fiber 9. The pressure chip 36 comprises a recessed cavity 39 covered by a diaphragm 38 forming the Fabry-Perot cavity 35. By way of non limiting example, a glass substrate 31 500 microns in thickness is first drilled with tiny holes 33 accommodating the fiber optic 9 to a thickness of 300 microns. It is understood by those skilled in the art that other combination of glass substrate thickness and drilling depth could also be used. The holes 33 can be drilled with an excimer laser tuned at 193 nm. The interest of drilling holes using an excimer laser is that the walls 32 of the holes 33 exhibit a deviation from the perpendicular limited to about 6 degrees. The quantity of adhesive 34 filling the hole is much less than with prior art and hence, the bending moment that is exerted as a result of adhesive swelling due to moisture has significant reduced impact on the variation of the Fabry-Perot cavity 35. By comparison with prior art, the drift is reduced by an order of magnitude, making this design perfectly well suited for medical applications.

In addition to a lower drift, the strength required to pull the pressure chip 36 off of the fiber optic 9 is much higher than with prior art sensors. This is another critical advantage as it makes the construction safer for patients.

For the light signal to be effectively coupled into the Fabry-Perot cavity 35, and back into the fiber optic 9, it is required to have a fairly neat surface 37 in the bottom of the hole. A rough surface 37 would distort the light beam, preventing effective in and out coupling. It is however difficult to achieve such a perfectly flat surface. The roughness of the surface can be mitigated by using an adhesive matching the refractive index of both the fiber optic and the glass substrate. A variety of biocompatible UV adhesives adequately matching both refractive indices are available from various manufacturers. By way of non limiting example, Dymax 141-M and Dymax 142-M are suitable adhesives.

Figure 5:
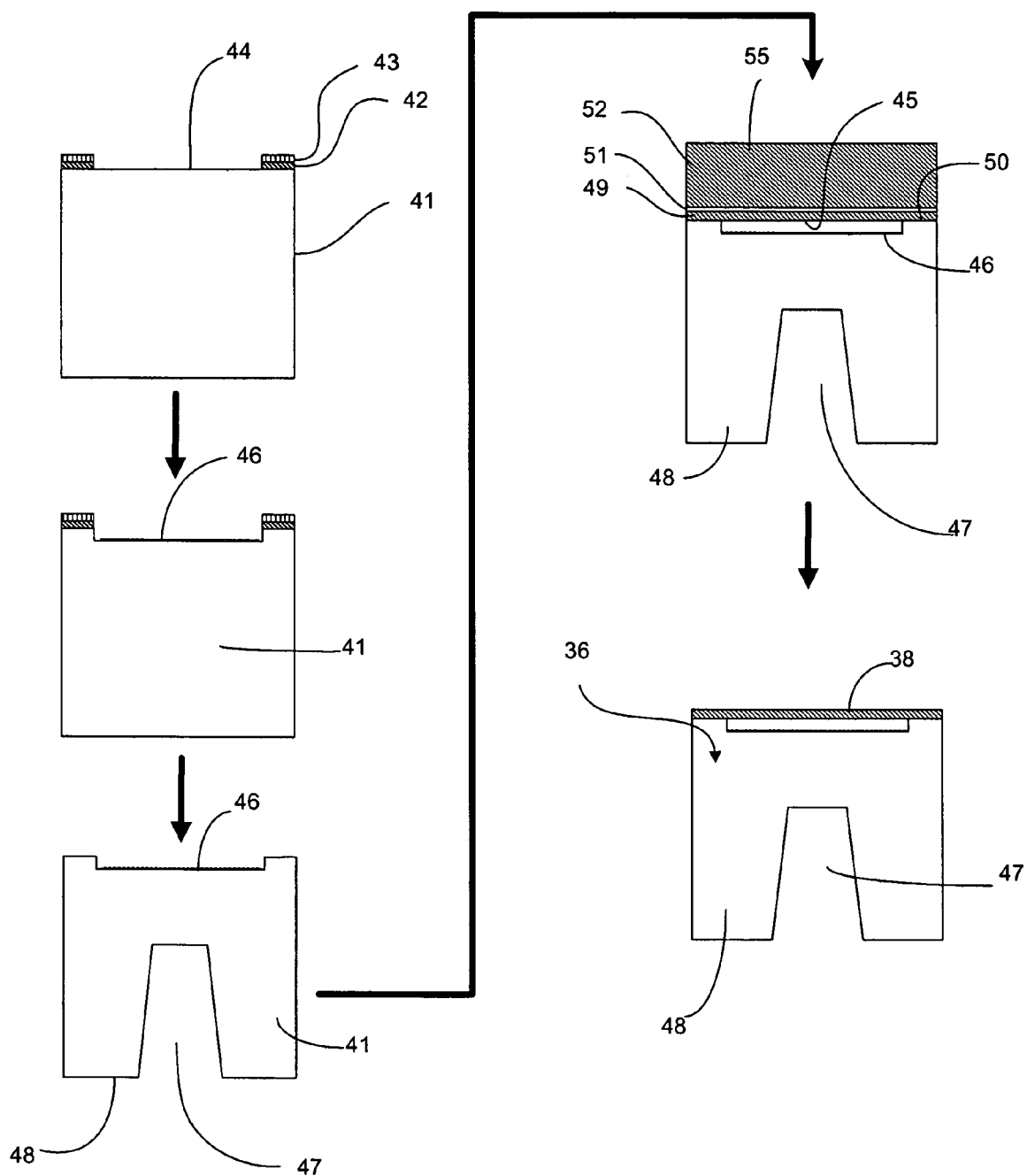
FIG. 5 is a series of schematic cross-section view illustrating a method of fabrication of a pressure chip, in accordance with a second embodiment of the present invention.

By way of non limiting example, a method for producing the pressure chip 36 of sensor 30 is shown in FIG. 5. A code 7740 glass substrate 41 500 microns thick is first coated with a layer of chrome 42 1000 Angstroms of thickness. This chrome layer will serve as a mask for etching the Fabry-Perot cavity 45 on the first surface 44 of the glass substrate. The chrome layer is then spin coated with a photoresist 43. The photoresist is then exposed with a mask that corresponds to the diameter of the Fabry-Perot cavity 45. Although the diameter of the Fabry-Perot cavity 45 can be of various sizes, a diameter of 300 microns has been found to be a good trade-off for minimizing the size of the cavity 45 while maintaining adequate deflection of the diaphragm as a function of the applied pressure. Once the photoresist 43 is exposed, the photoresist is developed, which then exposes selected portions of chrome. Exposed chrome is etched-off using chrome etch solution composed of one part of HCL and one part of glycerin. At this point, selected portions of the 7740 glass substrate 41 is ready for being etched down to the desired depth to form the Fabry-Perot cavity 45. Fabry-Perot cavities 45 of 300 microns diameter are etched down to a depth of 18 microns using a buffered HF solution composed of four parts of a mixture of 3 ml of water and 2 g of NH4F plus 1 part of 48% HF solution. Once the desired depth is reached, the substrate is removed and rinsed into de-ionized water for being coated with a semi-reflective mirror 46 constituting the first mirror of the Fabry-Perot cavity 45. The semi-reflective mirror 46 can be made of various oxide materials, such as a quarter wavelength of Ta2O5. The glass substrate 41 is now ready for being drilled on the second surface 48 of the substrate using an excimer laser. Once the holes 47 have been drilled, a silicon substrate 49 that contains the diaphragm 38 is anodically bonded on the first surface 50 of the glass substrate 41. The silicon substrate 49 will then have to be thinned to unveil the diaphragm 38.

The thickness of diaphragm 38 is usually controlled by using so-called etch stop layers. The most common etch stop makes use of heavily boron doped (p++) epi layer. A p++ layer is grown on the surface of a lightly doped silicon substrate to a thickness equal to the desired diaphragm thickness. Once anodically bonded, lightly doped portion of the silicon can be removed by mechanical grinding and chemical etching, such as in Ethylene Diamine Pyrocathecol (EDP) solution. Upon reaching the p++ layer, the etching process slows down by a factor of about 100. It is then not literally an etch stop process, but it is more like an etch slow process. Being an etch slow process, the thickness of the diaphragm is somewhat difficult to control. Also, one can hardly obtain a mirror-like surface because the grinded surface will be reproduced on the surface of the diaphragm, diminished by similar factor of 100. Also, it is not recommended to use p++ layer as a diaphragm as there may have internal residual stresses. Internal residual stresses along with irregular diaphragm surface contribute reducing the yield strength of the diaphragm, hence reducing the maximum pressure before diaphragm failure.

Another method for obtaining well controlled, mirror-like diaphragm makes use of silicon-on-insulator (SOI) silicon substrate 55. SOI substrate 55 is made of the thin silicon substrate 49 (device) thermally bonded to another thick silicon substrate 52 (handle), with an insulating silicon dioxide layer in-between 51. SOI wafers 55 are available off-the-shelf with various device 49 thicknesses. In this case, the silicon dioxide layer will act as a first etch-stop. By way of non-limiting example, once anodically bonded with device layer 49 face down against Pyrex™ substrate 41, the handle 52 can be removed by grinding a first portion of its total thickness, followed by a chemical etching using an EDP solution. Once the silicon dioxide 51 is reached, then the etching process slows-down by a factor of at least 10 000. The silicon dioxide layer 51 is finally removed using a HF-buffered solution. In this last case, the silicon is etched 10000 times slower than SiO2. As a result, the final pressure chip 36 then comprises a mirror-like diaphragm surface, with grinding reproduced irregularity reduced by a factor of more than 1000000, also providing perfect control of diaphragm thickness.

As will be obvious for someone skilled in the art, a reflective layer may be deposited on an internal surface of the diaphragm so as to obtain a Fabry-Perot cavity 45 with the desired characteristics (such as Finesse) and to prevent the formation of a parasitic cavity between the internal and external surfaces of the diaphragm. Such reflective layer can be a metallic layer such as, for example, a layer of chromium.

As a last step, the substrate is diced to single out the pressure chips 36. At this point, the pressure chips 36 are ready for receiving the optical fiber 9.

As will be obvious for someone skilled in the art, the Fabry-Perot cavity 45 of the pressure chip 36 can also be obtained by forming the recessed cavity 39 in the diaphragm 38 instead of forming the recessed cavity 39 in the glass substrate 41.

Figure 6:
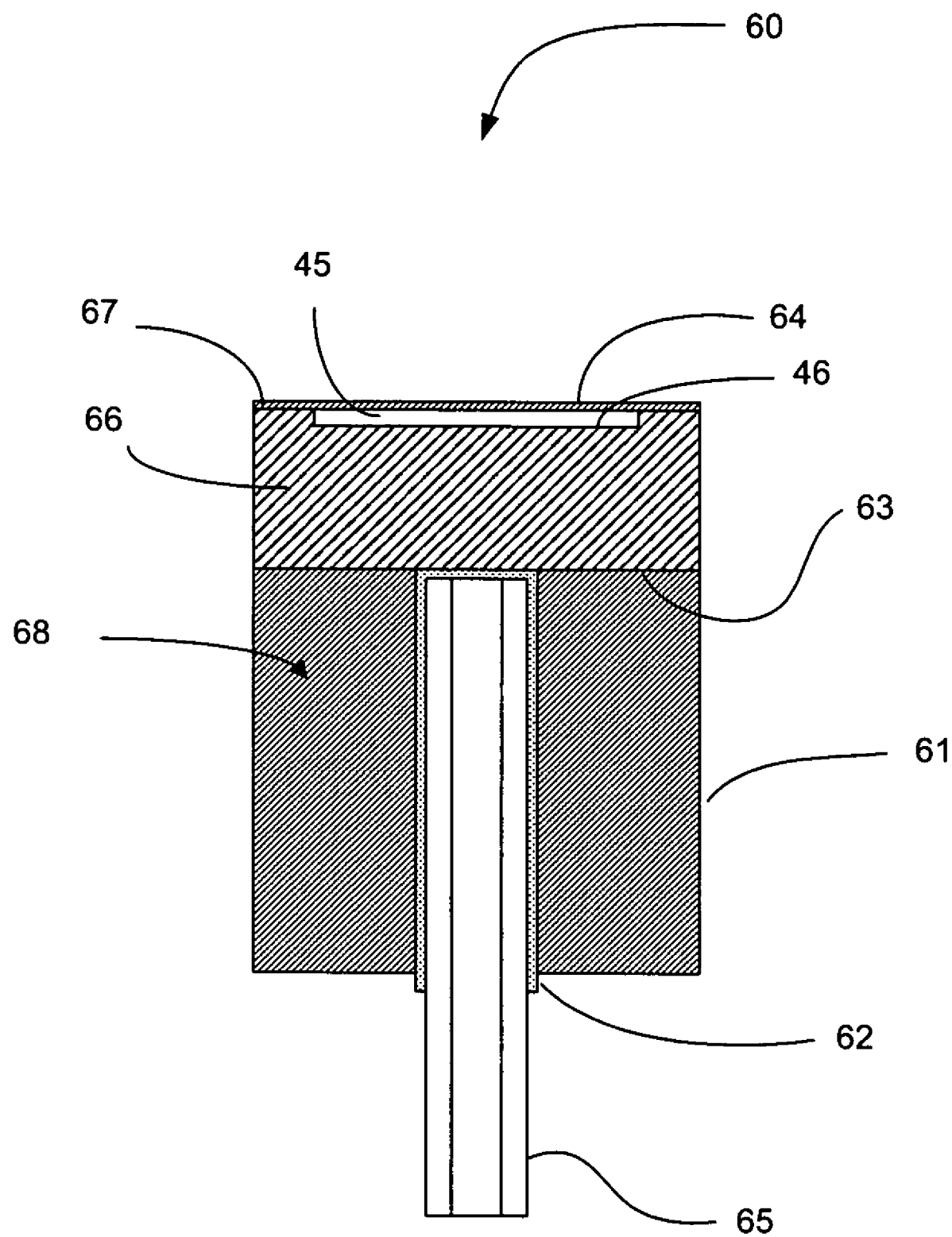
FIG. 6 is a schematic cross-section view of a fiber optic Fabry-Perot pressure sensor, in accordance with a third embodiment of the present invention.

An alternative fiber optic Fabry-Perot pressure sensor 60 is shown in FIG. 6. Sensor 60 comprises a pressure chip 68 coupled to an optical fiber 65. The use of a silicon substrate 61 300 microns thick etched with narrow etched hole 62 for receiving the optical fiber 65 differentiates this sensor 60 from sensor 30. It is indeed possible to etch vertical holes 62 into silicon substrates 61 with proper preferential etching and crystallography orientation. For example, one can etch similar holes 62 by selecting a silicon substrate 61 with (110) orientation. Preferential chemical etching using EDP, KOH, TMAH or dry etching using RIE or DRIE can produce vertical walls defined by the (111) planes as known by those skilled in the art. Although the silicon substrate 61 with etched holes 62 has the potential of exhibiting lower drift due to tighter perfectly vertical walls for accommodating the fiber optic 65, the hole 62 can very well be drilled using an excimer laser as with sensor 30. By way of non limiting example, those pressure chips 68 can be produced by first etching the Fabry-Perot cavity 45 followed by the deposition of a semi-reflective mirror 46. Silicon substrate 61 with etched holes 62 is then anodically bonded to the rear face 63 of the glass substrate 63. The diaphragm 64 can then be bonded to the other surface of the glass substrate 63. Techniques similar to those illustrated in FIG. 5 and described above for producing the diaphragm can be used to obtain final diaphragm 64.

Sensor 30 and sensor 60 may suffer from thermal sensitivity. At room temperature, the coefficient of thermal expansion (CTE) of silicon and Pyrex™ 7740 are $2.4 \times 10^{-6}$ C.$^{-1}$ and $3.1 \times 10^{-6}$ C.$^{-1}$ respectively. When temperature increases, the silicon diaphragm is brought into tension, hence moving outward.

Figure 7:
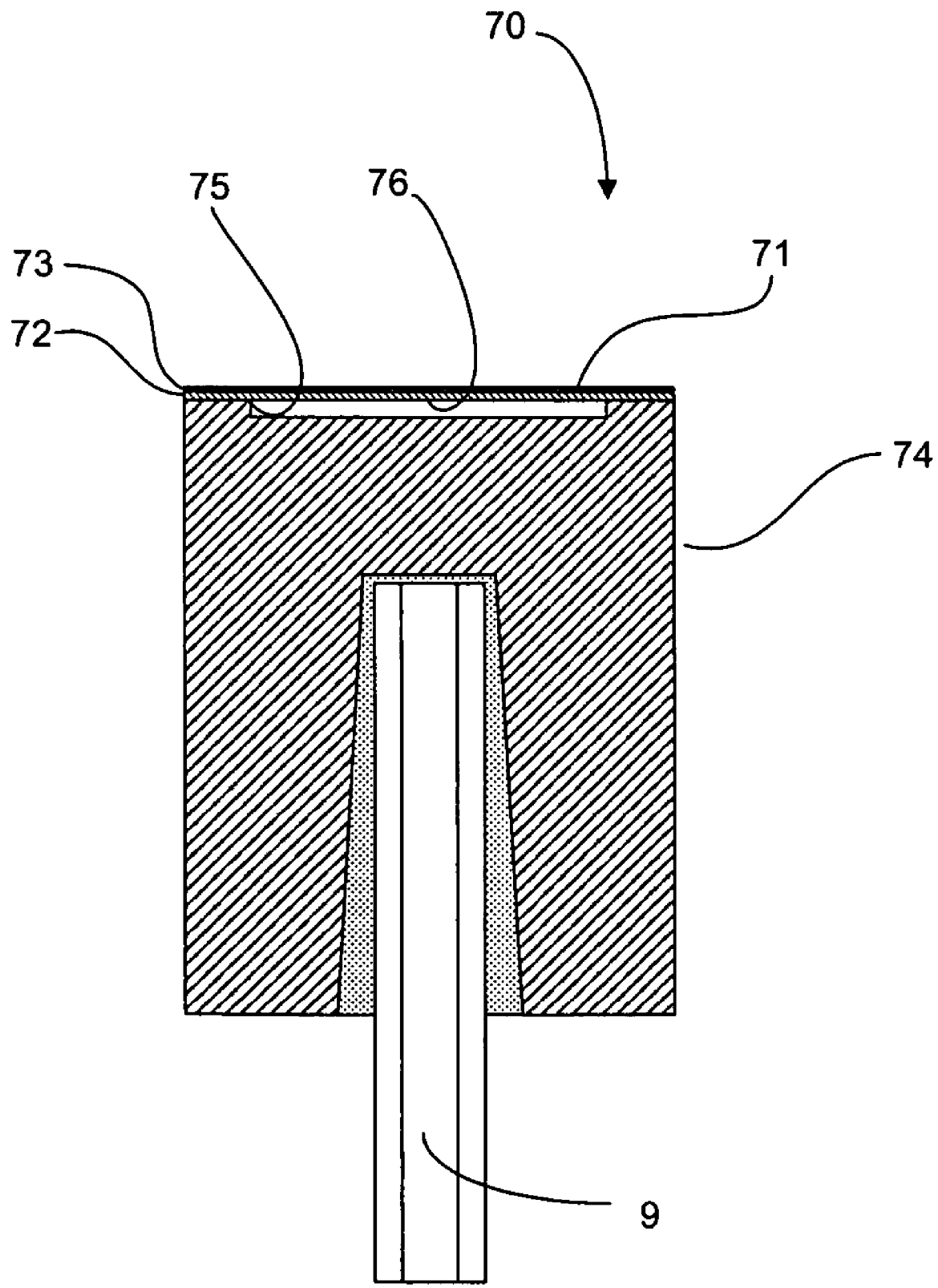
FIG. 7 is a schematic cross-section view of a fiber optic Fabry-Perot pressure sensor, in accordance with a fourth embodiment of the present invention.

A fiber optic Fabry-Perot pressure sensor 70 less sensitive to thermal shift, by means of thermal compensation, is shown in FIG. 7. Thermal compensation is achieved by depositing on the external surface 71 of the diaphragm 72 a material 73 exhibiting a CTE higher than the substrate 74. The higher the CTE of the compensating material, the thinner the layer can be. By way of non limiting example, a fairly thin layer of aluminum 73 can be deposited to compensate for thermal shift. For relatively small diaphragm deflection, bending stresses dominate tensile stresses. As a result, the outer surface of the diaphragm, when bowing downward, is in tension near the edge 75 of the diaphragm, while it is in compression in the center 76. Depositing a high CTE material on the whole surface of the diaphragm is not efficient because the central portion is in compression. For some specific designs, the deposition of a high CTE material may even accentuate the thermal shift.

Figure 8:
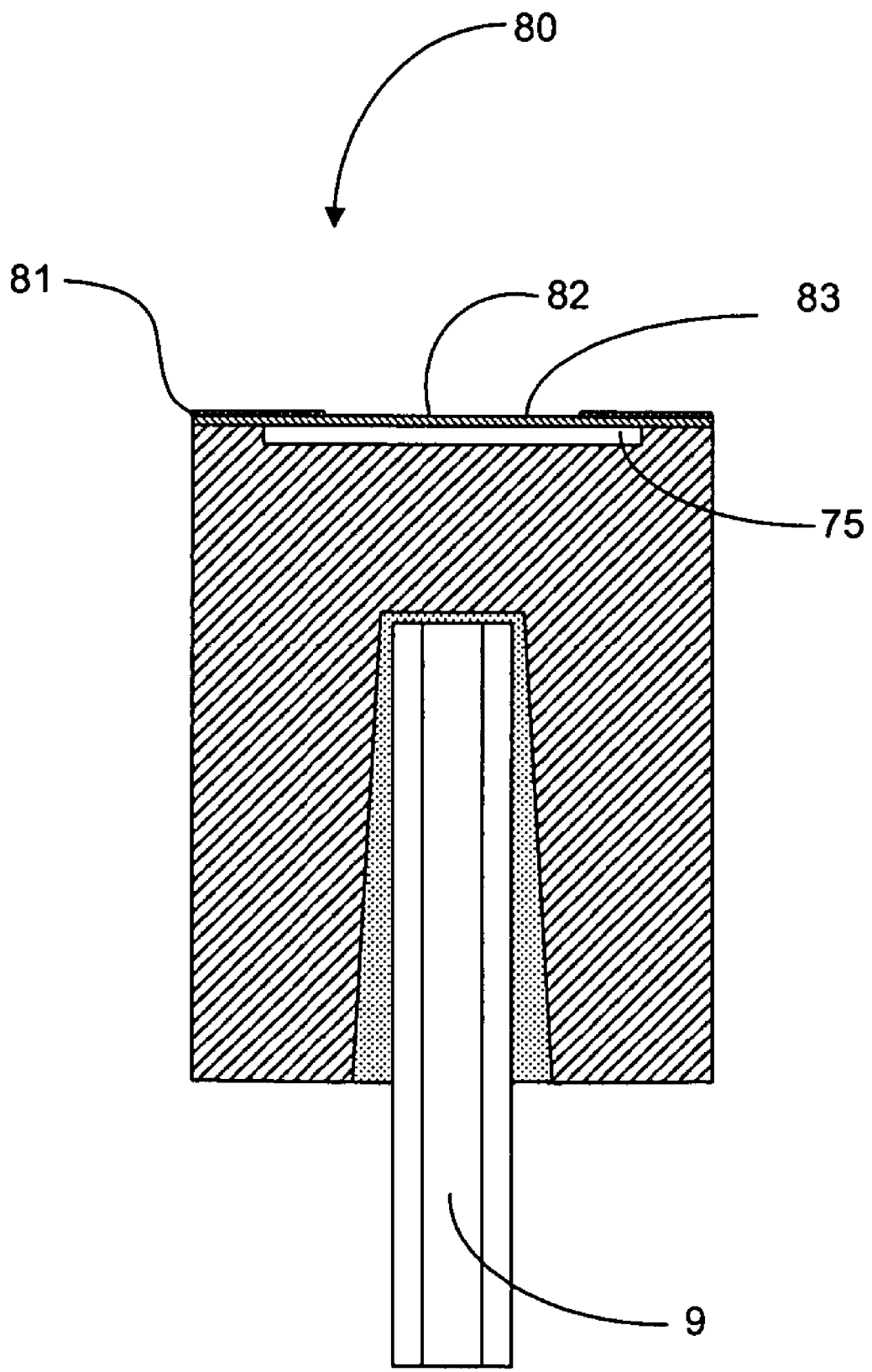
FIG. 8 is a schematic cross-section view of a fiber optic Fabry-Perot pressure sensor, in accordance with a fifth embodiment of the present invention.

For relatively small diaphragm deflection, which is the usual case for medical sensors, the sensor 80 shown in FIG. 8, has a diaphragm 83 on which a high CTE compensating material 81 have been deposited strictly on the edge portion of the diaphragm 83. For optimal results, as much as ⅔ of the central portion 82 of the diaphragm 83 should not contain any compensating material 81. The compensating material 81 should be deposited with a donut-like shape, the diameter of the center 82 being roughly equals to ⅔ times the total diameter of the effective diaphragm 83, which is the diameter of the recessed cavity 45. By way of non limiting example, an aluminum layer 81 of roughly 100 nanometers thick deposited on a Silicon diaphragm following the donut-like shape described above for a diaphragm having a diameter of 400 microns and thickness equals to 4 microns, would provide satisfactory thermal compensation.

Figure 9:
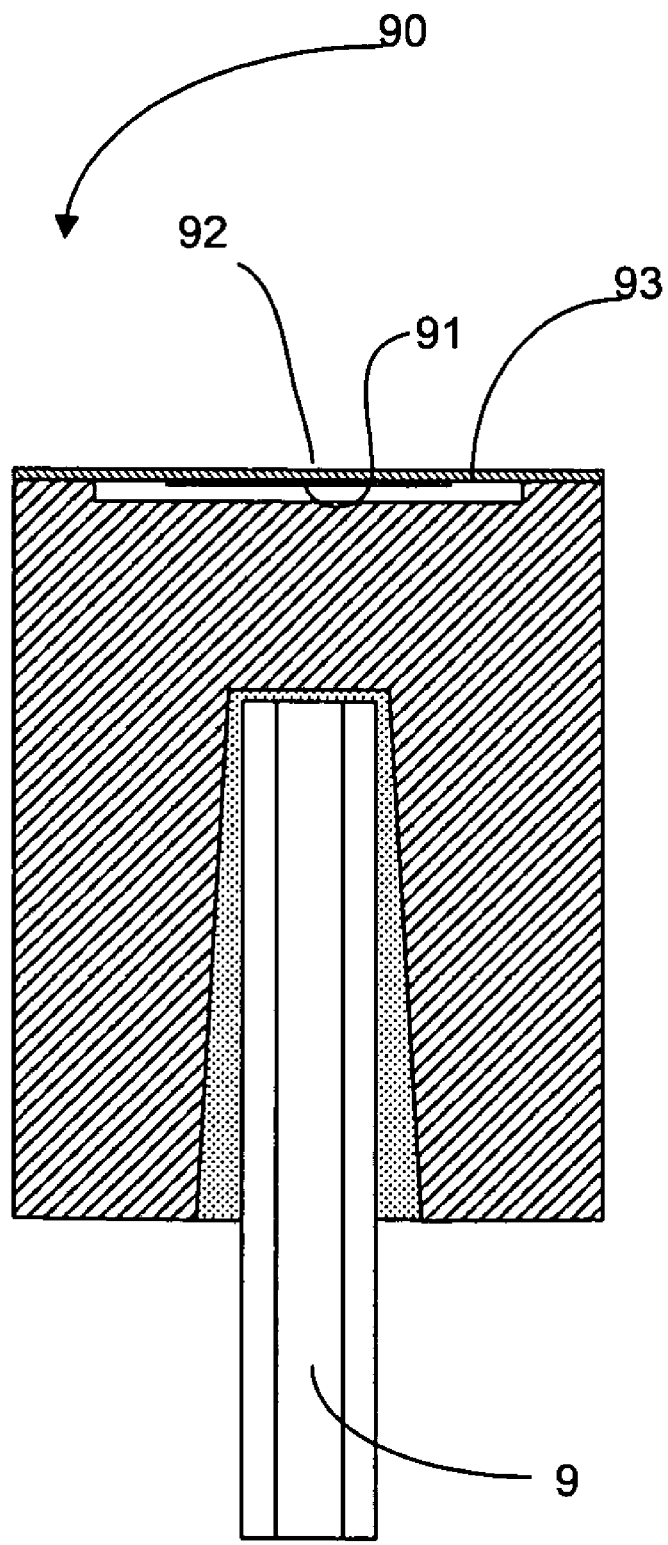
FIG. 9 is a schematic cross-section view of a fiber optic Fabry-Perot pressure sensor, in accordance with a sixth embodiment of the present invention.

As an alternative to sensor 80, Fabry Perot pressure sensor 90, illustrated in FIG. 9, has a high CTE material 91 deposited on the center of the internal surface. In one embodiment, the diameter of the layer 91 roughly equals ⅔ times the total diameter of the effective diaphragm 83. As compared to sensor 80, thinner high CTE material can be deposited on the central portion 92 of the diaphragm 93 to obtain similar thermal compensation. Compensating the thermal shift from the internal surface of the diaphragm 93 is more efficient than compensating from the external surface of the diaphragm 93. On the other hand, compensating from the external surface allows the tuning of the thickness, hence obtaining perfect compensation in all cases and hence increasing the yield. Tuning can be achieved by depositing a slightly thicker layer of compensating material 81, followed by post etching.

Although the use of low CTE material would be less efficient for compensating thermal shift, the difference in the CTE of silicon diaphragm and compensating material being limited to less than $2.4 \times 10^{-6}$ C.$^{-1}$, low CTE material can nonetheless be used for that purpose. From the above teaching, those skilled in the art will understand that thermal compensation can be obtained by depositing such low CTE material in ways opposite to those described herein above. For example, one could deposit a layer of low CTE silicon dioxide material on the central portion of the outer surface of the diaphragm, and oppositely, one could deposit the said low CTE material on the edge of the inner surface of the diaphragm.

In some occasion, sensors 30, 60, 80 and 90 may suffer from a change in sensitivity when immersed into a water based solution. We have indeed noticed that any exposed portion of the silicon diaphragm 38, 64, 72, 83, 93 is etched off when immersed into a water solution. It has been found that after being immersed into pure water for 4 to 6 days, silicon starts being etched at a rate of about 1 Angstrom per minute. Considering a diaphragm thickness of 3 to 4 microns, one can see that the sensitivity may change drastically at a fairly early stage of immersion. One can expect an even faster etching rate when immersed into blood, considering the blood pH. This change in sensitivity is also accompanied by an apparent drift because the pressure sensor is zeroed at atmospheric pressure. Although a change of sensitivity of say 0.5% appears to be within the limit of pressure sensor accuracy limit, the apparent pressure shift will in such a case be equivalent to 760 mmHg×0.5%=3.8 mmHg, then out of said required accuracy.

Another embodiment of the present invention consists in providing a protection against etching of the exposed silicon. By way of non-limiting example, one can deposit a thin layer of chromium for covering the exposed section, being understood that any other materials performing the same would eliminate silicon etching. For medical applications, it would be more desirable to deposit a thin layer of titanium or silicon oxide. The thickness of titanium required for protecting the silicon against etching, when immersed into water or blood, can be made fairly thin. To ease the production of the sensor, it would be very acceptable to cover the whole diaphragm with such a titanium layer. The titanium can be deposited on the external surface of the diaphragm prior to depositing the compensating material. For biocompatibility purposes, a preferred method involves the deposition of the titanium layer on top of both the exposed silicon diaphragm, and the high CTE temperature compensation material.

Although the present invention has been described hereinabove by way of specific embodiments thereof, it can be modified, without departing from the spirit and nature of the subject invention as defined herein.

The invention claimed is:

1. A Fabry-Perot pressure chip for use as a pressure sensor when interfaced to an optical fiber, the chip comprising:
   an integral body comprising a recessed cavity defining a first surface; and
   a diaphragm, separate and distinct from the integral body, covering the recessed cavity defining a first surface, and affixed to the body, the diaphragm defining a second surface; the first and second surfaces being separated by a distance and forming a Fabry-Perot cavity;
   the integral body further comprising a fiber receiving cavity opposed to and spaced from said recessed cavity and said first surface and defined by a fiber tip receiving surface and a side wall, the fiber receiving cavity for receiving an extremity of said optical fiber such that an adhesive receiving space is defined between an external side surface of the optical fiber and the side wall for receiving a small quantity of adhesive to secure the received extremity within said fiber receiving cavity, the side wall and the external side surface of the optical fiber defining an angle that is smaller than about fifteen degrees.

2. The Fabry-Perot pressure chip as claimed in claim 1, wherein the body comprises a borosilicate glass portion, the borosilicate glass portion comprising the first surface.

3. The Fabry-Perot pressure chip as claimed in claim 1, wherein the first surface comprises a semi-reflective layer.

4. The Fabry-Perot pressure chip as claimed in claim 1, wherein the diaphragm comprises silicon.

5. The Fabry-Perot pressure chip as claimed in claim 1, wherein the second surface comprises a layer of metallic material protective against damage due to the external environment.

6. The Fabry-Perot pressure chip as claimed in claim 5, wherein the layer of metallic material comprises a layer of chromium.

7. The Fabry-Perot pressure chip as claimed in claim 1, wherein the diaphragm is anodically bonded to the body.

8. The Fabry-Perot pressure chip as claimed in claim 1, further comprising:
   said optical fiber for relaying a light between an optical source and the Fabry-Perot cavity, an extremity of the optical fiber being inserted in the fiber receiving cavity of the chip and adhesively bound therein, for providing a fiber Fabry-Perot pressure sensor.

9. A Fabry-Perot pressure chip for use as a pressure sensor when interfaced to an optical fiber, the chip comprising:
   a body comprising a first surface, the body having a first coefficient of thermal expansion (first CTE), and
   a diaphragm covering the first surface and affixed to the body, the diaphragm having an internal and an external surface, the first and internal surfaces being separated by a distance and forming a Fabry-Perot cavity, the diaphragm having a second coefficient of thermal expansion (second CTE) different from the first CTE, the diaphragm further comprising a layer of material on one of said internal surface and said external surface and having a third coefficient of thermal expansion (third CTE) different from the first CTE and from the second CTE, said third CTE being selected such that a thermal expansion of said layer of material causes a mechanical stress on the diaphragm that counters a mechanical stress induced in the diaphragm due to thermal expansion mismatch between the body and the diaphragm, in order to compensate an undesirable deformation of the diaphragm due to temperature and wherein the layer of the material is disposed on one of a central portion and a peripheral portion of the diaphragm.

10. The Fabry-Perot pressure chip of claim 9, wherein the second CTE is lower than the first CTE, wherein the third CTE is lower than the first OTE and wherein the layer of the material is disposed on one of a central portion of the external surface and a peripheral portion of the internal surface.

11. The Fabry-Perot pressure chip of claim 10, wherein the body is in borosilicate glass and the layer is in $SiO_2$.

12. The Fabry-Perot pressure chip of claim 9, wherein the second OTE is lower than the first CTE, wherein the third CTE is higher than the first CTE, and wherein the layer of the material is disposed on one of a peripheral portion of the external surface and a central portion of the internal surface.

13. The Fabry-Perot pressure chip of claim 12, wherein the body is in borosilicate glass and the layer is in aluminum.

14. The Fabry-Perot pressure chip of claim 9, wherein the body comprises a fiber receiving cavity for receiving and securing therein an extremity of an optical fiber, the optical fiber for relaying an optical signal to the Fabry-Perot cavity.

15. The Fabry-Perot pressure chip as claimed in claim 14, further comprising:

said optical fiber for relaying a light between an optical source and the Fabry-Perot cavity, an extremity of the optical fiber being inserted in the fiber receiving cavity of the chip and adhesively bound therein, for providing a fiber Fabry-Perot pressure sensor.

* * * * *